(12) United States Patent
McQuillan et al.

(10) Patent No.: US 9,339,369 B2
(45) Date of Patent: May 17, 2016

(54) REINFORCED BIOLOGICAL TISSUE

(75) Inventors: David J. McQuillan, Doylestown, PA (US); John R. Harper, Jamison, PA (US); Christopher T. Wagner, Easton, PA (US); E. Skott Greenhalgh, Wyndmoor, PA (US)

(73) Assignee: LifeCell Corporation, Branchburg, NJ (US)

( * ) Notice: Subject to any disclaimer, the term of this patent is extended or adjusted under 35 U.S.C. 154(b) by 713 days.

(21) Appl. No.: 11/746,557

(22) Filed: May 9, 2007

(65) Prior Publication Data

US 2008/0027542 A1 Jan. 31, 2008

Related U.S. Application Data

(60) Provisional application No. 60/799,102, filed on May 9, 2006.

(51) Int. Cl.
*A61F 2/08* (2006.01)
*A61F 2/02* (2006.01)
*A61L 27/40* (2006.01)
*A61L 27/00* (2006.01)
*A61L 27/36* (2006.01)

(52) U.S. Cl.
CPC .............. *A61F 2/08* (2013.01); *A61L 27/3683* (2013.01); *A61L 27/40* (2013.01); *A61F 2/02* (2013.01); *A61F 2/0805* (2013.01); *A61F 2/0811* (2013.01); *A61L 27/00* (2013.01); *A61L 27/3662* (2013.01)

(58) Field of Classification Search
CPC ..... A61L 27/40; A61L 27/3683; A61L 27/00; A61L 27/28; A61L 27/3662; A61F 2/08; A61F 2/0805; A61F 2/0811; A61F 2/02
USPC ............ 623/13.11–13.2, 23.72, 23.74, 23.76; 606/151
See application file for complete search history.

(56) References Cited

U.S. PATENT DOCUMENTS

| | | | |
|---|---|---|---|
| 3,463,158 A | * | 8/1969 | Schmitt et al. ............... 606/154 |
| 4,599,084 A | | 7/1986 | Nashef |
| 4,633,873 A | * | 1/1987 | Dumican et al. ............. 606/151 |
| 5,002,583 A | | 3/1991 | Pitaru et al. |
| 5,078,744 A | | 1/1992 | Chvapil |

(Continued)

OTHER PUBLICATIONS

Scott A. Klein et al. "Tendon Graft Fixation in ACL Reconstruction" *Acta Ortho Scand*, 75(1): 84-88 (2004).

(Continued)

*Primary Examiner* — Jing Ou
(74) *Attorney, Agent, or Firm* — McCarter & English, LLP; Matthew R. Van Eman (57) ABSTRACT

The present invention provides for an implantable medical device comprising a hybrid composite material including a first biological component such as an acellular tissue matrix and a second non-biological component for strengthening the device after implantation.

20 Claims, 6 Drawing Sheets

(56) References Cited

U.S. PATENT DOCUMENTS

| | | | |
|---|---|---|---|
| 5,116,372 A | 5/1992 | Laboureau | |
| 5,425,766 A | 6/1995 | Bowald | A61F 2/08 |
| 5,514,181 A * | 5/1996 | Light et al. | 623/13.18 |
| 5,595,621 A * | 1/1997 | Light et al. | 156/80 |
| 5,855,619 A | 1/1999 | Caplan et al. | |
| 6,592,622 B1 | 7/2003 | Ferguson | |
| 6,884,428 B2 | 4/2005 | Binette et al. | |
| 6,946,003 B1 * | 9/2005 | Wolowacz et al. | 623/23.72 |
| 7,252,832 B1 | 8/2007 | Stone et al. | |
| 2003/0035843 A1 * | 2/2003 | Livesey et al. | 424/549 |
| 2004/0034418 A1 | 2/2004 | Li et al. | A61F 2/08 |
| 2004/0078077 A1 * | 4/2004 | Binette et al. | 623/13.17 |
| 2004/0267362 A1 * | 12/2004 | Hwang et al. | 623/13.15 |
| 2005/0159822 A1 | 7/2005 | Griffey et al. | A61F 2/02 |
| 2007/0162124 A1 * | 7/2007 | Whittaker | 623/13.14 |

OTHER PUBLICATIONS

Charles E. Butler et al. "Reduction of Abdominal Adhesions Using Composite Collagen-GAG Implants for Ventral Hernia Repair" *Plast Reconstr Surg.*, Aug;114(2):464-73 (2004).

Charles E. Butler et al. "Reduction of Adhesions with Composite AlloDerm/Polypropylene Mesh Implants for Abdominal Wall Reconstruction" *J Biomed Mater Res.*, 58(1):75-80 (2001).

\* cited by examiner

REINFORCED BIOLOGICAL TISSUE

CLAIM OF PRIORITY

This application claims priority to U.S. Provisional Application No. 60/799,102, filed May 9, 2006, the disclosure of which is incorporated herein by reference in its entirety.

TECHNICAL HELD

The present invention generally relates to tissue matrices for tissue repair, and more particularly to hybrid acellular tissue matrices in combination with synthetic biocompatible material for tissue repair.

BACKGROUND

Ligament and tendon replacement in mammals has long sought a material that approximates the load transmission and performance of the native ligament and tendon structures. Synthetic ligaments and tendons have been made from steel, polyester, polyurethane, polyethelene, Nylons, polytetrafluoroethylene, carbon fiber and other man made materials. Combinations of any one or more of the aforementioned materials have also been used to manufacture synthetic ligament tissue. However, synthetics typically experience decreasing functional capability over time, and can wear out, fray and/or particulate in relatively short time periods (e.g. about, 1, 2, 3 or 4 years) after implantation.

As an alternative to synthetic materials, natural ligament or tendon tissue harvested from a donor site, such as autografts and/or cadaveric tissue grafts (i.e. allografts), may also be used in ligament or tendon replacement procedures. As with synthetic materials, for both autografts and allografts, long-term recovery of functional parameters (e.g., failure load, linear and tangential stiffness, failure stress, and strain at failure) remain significantly reduced compared to native ligament, tendon or other soft tissue structures.

Autografts come from donor sites of the recipient of the graft itself. For example, in ACL (anterior cruciate ligament) reconstruction, a part of the patient's own patellar ligament or hamstring tendon can be used to replace the torn ACL.

A cadaveric tissue graft can be placed in the site of the torn ACL, for example, without donor site morbidity associated with autograft harvesting. Although cadaver tissues are typically treated in some way to reduce any foreign body reactions, they can transmit disease. In most cases allografts heal more slowly and tend to have significantly higher failure rates than autografts.

Man made and cadaveric tissue grafts are advantageous over autografts because they do not have donor site morbidity and pain, both immediate and long-term, associated with harvesting autografts.

Accordingly, there is a need for a material for ligament, tendon and other soft tissue repair and replacement that is free of donor site morbidity associated with autografts, has improved failure rates over traditional allografts and synthetic tissues, and better approximates native tissue biomechanical performance.

The discussion of the background to the invention herein is included to explain the context of the invention. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

The present invention is directed to an implantable medical device comprising a hybrid synthetic and natural tissue repair and replacement material addressing the need of reducing donor site morbidity, improving failure rates and/or better approximating native tissue performance in ligament, tendon, and other soft tissue repair and replacement procedures.

In particular, an implementation of the present invention comprises a composite material with a first biological component that includes a biomatrix and a second non-biolgical component. Further implementations comprise a second non-biological component having a higher load capacity than the first component at the time of implantation. Various implementations of the present invention are particularly applicable to ligament, tendon and other soft tissue repair and replacement.

Yet another implementation of the present invention comprises an implantable medical device having a composite material comprising a first biological component having a biomatrix, and a second non-biological component. The first component overlays the second component for at least a portion of the composition of the composite material.

A further implementation of the present invention comprises an implantable medical device having a composite material comprising a first biological component having a biomatrix, and a second non-biological component. The first component overlays the second component for substantially all of the composite material.

Still another implementation of the present invention comprises an implantable medical device having a composite material comprising a first biological component comprising an acellular tissue matrix, and a second non-biological component.

Another implementation of the present invention comprises an implantable medical device having a composite material comprising a first biological component having a biomatrix, and a second non-biological component. The first component is applied to the second component as a coating, a paste, a powder, or a liquid.

A further implementation of the present invention comprises an implantable medical device having a composite material comprising a first biological component having a biomatrix, and a second non-biological component that has a higher load capacity than the first component at the time of implantation.

An even further implementation of the present invention comprises an implantable medical device having a composite material comprising a first biological component having a biomatrix, and a second non-biological component. The first component has a higher load capacity than the second component after implantation and following growth of native cells within the biomatrix of the first component.

Still another implementation of the present invention comprises an implantable medical device having a composite material comprising a first biological component having a biomatrix, and a second non-biological component comprising a bioabsorbable polymer.

And yet another implementation of the present invention comprises an implantable medical device having a composite material comprising a first biological component having a biomatrix, and a second non-biological component comprising a biocompatible metal.

An additional implementation of the present invention comprises an implantable medical device having a composite material comprising a first biological component having a biomatrix, and a second non-biological component comprising polyhydroxybutyrate, polyactic acid, polyactideglycolide acid, polydioxanome or polycaprolactone.

A further implementation of the present invention comprises an implantable medical device having a composite material comprising a first biological component having a biomatrix, and a second non-biological component of contiguous material.

Still a further implementation of the present invention comprises an implantable medical device having a composite material comprising a first biological component having a biomatrix, and a second non-biological component. And the second component is a textile including non-biologic material, the textile being a knit, a weave, a braid, a nonwoven structure, or a combination of knit, weave, braid or nonwoven structures. The textile can further include a monofilament of non-biological material or a braided or spun yarn of non-biological material.

Another implementation of the present invention comprises an implantable medical device having a composite material comprising a first biological component having a biomatrix, and a second non-biological component. The first component is applied to the second component as a coating, a paste, a powder, or a liquid.

Still a further implementation of the present invention comprises an implantable medical device having a composite material comprising a first biological component having a biomatrix, and a second non-biological component. The composite material forms a sheet, a cylinder, a solid tube, a hollow tube or a rolled sheet.

And a still further implementation of the present invention comprises an implantable medical device having a composite material comprising a first biological component having a biomatrix, a second non-biological component; and a tether portion.

Additionally a method is provided for implanting a medical device wherein a composite material is provided. The composite material includes a first biological component having a biomatrix to facilitate in-growth of native cells and a second non-biological component to provide strength to the medical device at the time of implantation and before significant native cell in-growth through the biomatrix of the first component. The composite material is anchored proximal to the implant site. The composite material may be anchored to the implant site from within the composite material.

DETAILED DESCRIPTION

The present invention is directed to a "hybrid" composite material comprising both biologic and non-biologic components suitable for use as a tissue implant or replacement for a ligament, tendon or soft tissue structure. The hybrid tissue is constructed as a composite of at least two materials, for example, a man-made, non-biologic component (e.g., a synthetic polymer) and a biological component (e.g., a biomatrix). In an implementation the man-made non-biologic component is intimately combined with the biological component to create a composite hybrid prosthetic tissue that leverages the advantageous properties of each constituent material.

The non-biologic component, such as a polymer, is designed to provide appropriate strength and stiffness to the hybrid composite structure immediately after implantation and to transmit higher loads over traditional biologic implants when the hybrid ligament is implanted. Also, the non-biologic component transmits some load and motion to the biological component. The biological component is designed to create a longer term healing response. The motion/load distribution between the synthetic component and the biologic component of the hybrid material contributes to an environment suited for tissue healing. The biological component via a biomatrix facilitates a complex process of becoming or transforming from a basic biological tissue to a tissue similar to the native tissue being replaced (e.g., a ligament-like tissue) by encouraging or allowing the in-growth of native cells within the matrix structure of the biological component.

Various implementations can include one or more layers of biologic and non-biologic components resulting in the hybrid composite material contemplated herein. Before describing the composite structure, the individual components will be described in greater detail.

Biological Component:

Biological components of an implementation of the present invention can generally be any biological material (e.g., whole tissue or tissue-derived material) with the advantageous properties described herein. Particularly useful biological components are biomatrices including acellular tissue matrices.

As used herein, an "acellular tissue matrix" ("ATM") is a tissue-derived biomatrix structure that is made from any of a wide range of collagen-containing tissues by removing all, or substantially all, viable cells and all detectable subcellular components and/or debris generated by killing cells. As used herein, an ATM lacking "substantially all viable cells" is an ATM in which the concentration of viable cells is less than 1% (e.g., less than: 0.1%; 0.01%; 0.001%; 0.0001%; 0.00001%; or 0.000001%) of that in the tissue or organ from which the ATM was made.

The ATM useful for the invention preferably, but not necessarily, lacks, or substantially lacks, an epithelial basement membrane. The epithelial basement membrane is a thin sheet of extracellular material contiguous with the basilar aspect of epithelial cells. Sheets of aggregated epithelial cells form an epithelium. Thus, for example, the epithelium of skin is called the epidermis, and the skin epithelial basement membrane lies between the epidermis and the dermis. The epithelial basement membrane is a specialized extracellular matrix that provides a barrier function and an attachment surface for epithelial-like cells; however, it does not contribute any significant structural or biomechanical role to the underlying tissue (e.g., dermis). Unique components of epithelial basement membranes include, for example, laminin, collagen type VII, and nidogen. The unique temporal and spatial organizations of the epithelial basement membrane distinguish it from, e.g., the dermal extracellular matrix. The presence of the epithelial basement membrane in an ATM of the invention could be disadvantageous in that the epithelial basement membrane likely contains a variety of species-specific components that would elicit the production of antibodies, and/or bind to preformed antibodies, in xenogeneic graft recipients of the acellular matrix. In addition, the epithelial basement membrane can act as a barrier to diffusion of cells and/or soluble factors (e.g., chemoattractants) and to cell infiltration. Its presence in ATM grafts can thus significantly delay formation of new tissue from the acellular tissue matrix in a recipient animal. As used herein, an ATM that "substantially lacks" an epithelial basement membrane is an acellular tissue matrix containing less than 5% (e.g., less than: 3%; 2%; 1%; 0.5%; 0.25%; 0.1%; 0.01%; 0.001%; or even less than 0.0001%) of the epithelial basement membrane possessed by the corresponding unprocessed tissue from which the acellular tissue matrix was derived.

Biological functions retained by the ATM include cell recognition and cell binding as well as the ability to support cell spreading, cell proliferation, cellular in-growth and cell differentiation. Such functions are provided by undenatured collagenous proteins (e.g., type I collagen) and a variety of non-collagenous molecules (e.g., proteins that serve as ligands for either molecules such as integrin receptors, molecules with high charge density such as glycosaminoglycans (e.g., hyaluronan) or proteoglycans, or other adhesins). Structural functions retained by useful acellular matrices include maintenance of histological architecture, maintenance of the three-dimensional array of the tissue's components and physical characteristics such as strength, elasticity, and durability, defined porosity, and retention of macromolecules. The efficiency of the biological functions of an ATM can be measured, for example, by the ability of the ATM to support cell proliferation and is at least 50% (e.g., at least: 50%; 60%; 70%; 80%; 90%; 95%; 98%; 99%; 99.5%; 100%; or more than 100%) of that of the native tissue or organ from which the ATM is made.

It is not necessary that the grafted matrix material be made from tissue that is identical to the surrounding host tissue but should simply be amenable to being remodeled by infiltrating cells such as differentiated cells of the relevant host tissue, stem cells such as mesenchymal stem cells, or progenitor cells. Remodeling is directed by the above-described ATM components and signals from the surrounding host tissue (such as cytokines, extracellular matrix components, biomechanical stimuli, and bioelectrical stimuli). The presence of mesenchymal stem cells in the bone marrow and the peripheral circulation has been documented in the literature and shown to regenerate a variety of musculoskeletal tissues [Caplan (1991) J. Orthop. Res. 9:641-650; Caplan (1994) Clin. Plast. Surg. 21:429-435; and Caplan et al. (1997) Clin Orthop. 342:254-269]. Additionally, the graft must provide some degree (greater than threshold) of tensile and biomechanical strength during the remodeling process.

It is understood that the ATM can be produced from any collagen-containing soft tissue and muscular skeleton (e.g., dermis, fascia, pericardium, dura, umbilical cords, placentae, cardiac valves, ligaments, tendons, vascular tissue (arteries and veins such as saphenous veins), neural connective tissue, urinary bladder tissue, ureter tissue, or intestinal tissue), as long as the above-described properties are retained by the matrix. Moreover, the tissues in which the hybrid matrices containing the ATM are placed include essentially any tissue that can be remodeled by invading or infiltrating cells. Relevant tissues include, without limitation, skeletal tissues such as bone, cartilage, ligaments, fascia, and tendon. Other tissues in which any of the above allografts can be placed include, without limitation, skin, gingiva, dura, myocardium, vascular tissue, neural tissue, striated muscle, smooth muscle, bladder wall, ureter tissue, intestine, and urethra tissue.

Furthermore, while an ATM will generally have been made from one or more individuals of the same species as the recipient of the ATM graft, this is not necessarily the case. Thus, for example, an ATM can have been made from a porcine tissue and be implanted in a human patient. Species that can serve as recipients of ATM and donors of tissues or organs for the production of the ATM include, without limitation, humans, non-human primates (e.g., monkeys, baboons, or chimpanzees), porcine, bovine, horses, goats, sheep, dogs, cats, rabbits, guinea pigs, gerbils, hamsters, rats, or mice. Of particular interest as donors are animals (e.g., pigs) that have been genetically engineered to lack the terminal α-galactose moiety. For descriptions of appropriate animals see co-pending U.S. application Ser. No. 10/896,594 and U.S. Pat. No. 6,166,288, the disclosures of all of which are incorporated herein by reference in their entirety.

Moreover, rather than using such genetically engineered animals as donors, appropriate tissues and organs can be treated, before or after decellularization, with the enzyme α-galactosidase which removes terminal α-galactose (α-gal) moieties from saccharide chains on, for example, glycoproteins. Methods of treating tissue with α-galactosidase to remove these moieties are described in, for example, U.S. Pat. No. 6,331,319, the disclosure of which is incorporated herein by reference in their entirety.

In an implementation, either before or after the soft tissue cells are killed in the ATM, the collagen-containing material is subjected to in vitro digestion of the collagen-containing material with one or more glycosidases, and particularly galactosidases, such as α-galactosidase. In particular, α-gal epitopes are eliminated by enzymatic treatment with α-galactosidases, as shown in the following reaction:

The N-acetyllactosamine residues are epitopes that are normally expressed on human and mammalian cells and thus are not immunogenic. The in vitro digestion of the collagen-containing material with glycosidases is accomplished by various methods. For example, the collagen-containing material can be soaked or incubated in a buffer solution containing glycosidase. Alternatively, a buffer solution containing the glycosidase can be forced under pressure into the collagen-containing material via a pulsatile lavage process.

Elimination of the α-gal epitopes from the collagen-containing material diminishes the immune response against the collagen-containing material. The α-gal epitope is expressed in nonprimate mammals and in New World monkeys (monkeys of South America) as $1\times10^6$-$35\times10^6$ epitopes per cell, as well as on macromolecules such as proteoglycans of the extracellular components. U. Galili et al., J. Biol. Chem. 263: 17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., Infect. Immun. 56: 1730 (1988); R. M. Hamadeh et al., J. Clin. Invest. 89: 1223 (1992). Since nonprimate mammals (e.g., pigs) produce α-gal epitopes, xenotransplantation by injection of collagen-containing material from these mammals into primates results in rejection because of primate anti-Gal binding to these epitopes on the collagen-containing material. The binding results in the destruction of the collagen-containing material by complement fixation and by antibody dependent cell cytotoxicity. U. Galili et al., Imnunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-gal antibodies. Accordingly, the substantial elimination of α-gal epitopes from cells and from extracellular components of the collagen-containing material, and the prevention of reexpression of cellular α-gal epitopes can diminish the immune response against the collagen-containing material associated with anti-gal antibody binding to α-gal epitopes.

The form in which the ATM is provided will depend on the tissue or organ from which it is derived and on the nature of the recipient tissue or organ, as well as the nature of the damage or defect in the recipient tissue or organ. Thus, for example, a matrix derived from a heart valve can be provided as a whole valve, as small sheets or strips, as pieces cut into any of a variety of shapes and/or sizes, or in a particulate form. The same concept applies to ATM produced from any of the above-listed tissues and organs. It is understood that an ATM useful for the invention can be made from a recipient's own collagen-based tissue.

The ATM can be produced by any of a variety of methods. All that is required is that the steps used in their production result in matrices with the above-described biological and structural properties. Particularly useful methods of production include those described in U.S. Pat. Nos. 4,865,871; 5,366,616, and 6,933,326, and copending U.S. application Ser. No. 10/165,790, published as U.S. Patent Application Pub. No. US 2003/0035843 A1, and Ser. No. 10/896,594, published as U.S. Patent Application Pub. No. US 2005/0028228 A1, all of which are incorporated herein by reference in their entirety.

In brief, the steps involved in the production of an ATM generally include harvesting the tissue from a donor (e.g., a human cadaver or any of the above-listed mammals), chemical treatment so as to stabilize the tissue and avoid biochemical and structural degradation together with, or followed by, cell removal under conditions which similarly preserve biological and structural function. After thorough removal of dead and/or lysed cell components that may cause inflammation as well as any bioincompatible cell-removal agents, the matrix can be treated with a cryopreservation agent and cryopreserved and, optionally, freeze dried, again under conditions necessary to maintain the described biological and structural properties of the matrix. After freeze drying, the tissue can, optionally, be pulverized or micronized to produce a particulate ATM under similar function-preserving conditions. After cryopreservation or freeze-drying (and optionally pulverization or micronization), the ATM can be thawed or rehydrated, respectively. All steps are generally carried out under aseptic, preferably sterile, conditions.

The initial stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution generally contains an appropriate buffer, one or more antioxidants, one or more oncotic agents, one or more antibiotics, one or more protease inhibitors, and in some cases, a smooth muscle relaxant.

The tissue is then placed in a processing solution to remove viable cells (e.g., epithelial cells, endothelial cells, smooth muscle cells, and fibroblasts) from the structural matrix without damaging the basement membrane complex or the biological and structural integrity of the collagen matrix. The processing solution generally contains an appropriate buffer, salt, an antibiotic, one or more detergents (e.g., Triton-x-100, sodium deoxycholate, polyoxyethylene (20) sorbitan monooleate), one or more agents to prevent cross-linking, one or more protease inhibitors, and/or one or more enzymes. Treatment of the tissue must be (a) with a processing solution containing active agents at a concentration and (b) for a time period such that the structural integrity of the matrix is maintained.

Alternatively, the tissue can be cryopreserved prior to undergoing water replacement. If so, after decellularization, the tissue is incubated in a cryopreservation solution. This solution generally contains one or more cryoprotectants to minimize ice crystal damage to the structural matrix that could occur during freezing. If the tissue is to be freeze dried, the solution will generally also contain one or more dry-protective components, to minimize structural damage during drying and may include a combination of an organic solvent and water which undergoes neither expansion nor contraction during freezing. The cryoprotective and dry-protective agents can be the same one or more substances. If the tissue is not going to be freeze dried, it can be frozen by placing it (in a sterilized container) in a freezer at about $-80°$ C., or by plunging it into sterile liquid nitrogen, and then storing at a temperature below $-160°$ C. until use. The tissue sample can be thawed prior to use by, for example, immersing a sterile non-permeable vessel (see below) containing the sample in a water bath at about $37°$ C. or by allowing the tissue to come to room temperature under ambient conditions.

If the tissue is to be frozen and freeze dried, following incubation in the cryopreservation solution, the tissue is packaged inside a sterile vessel that is permeable to water vapor yet impermeable to bacteria, e.g., a water vapor permeable pouch or glass vial. One side of a preferred pouch consists of medical grade porous Tyvek® membrane, a trademarked product of DuPont Company of Wilmington, Del. This membrane is porous to water vapor and impervious to bacteria and dust. The Tyvek membrane is heat sealed to an impermeable polyethylene laminate sheet, leaving one side open, thus forming a two-sided pouch. The open pouch is sterilized by irradiation prior to use. The tissue is aseptically placed (through the open side) into the sterile pouch. The open side is then aseptically heat sealed to close the pouch. The packaged tissue is henceforth protected from microbial contamination throughout subsequent processing steps.

The vessel containing the tissue is cooled to a low temperature at a specified rate which is compatible with the specific cryoprotectant formulation to minimize the freezing damage. See U.S. Pat. No. 5,336,616 for examples of appropriate cooling protocols. The tissue is then dried at a low temperature under vacuum conditions, such that water vapor is removed sequentially from each ice crystal phase.

At the completion of the drying of the samples in the water vapor permeable vessel, the vacuum of the freeze drying apparatus is reversed with a dry inert gas such as nitrogen, helium or argon. While being maintained in the same gaseous environment, the semipermeable vessel is placed inside an impervious (i.e., impermeable to water vapor as well as microorganisms) vessel (e.g., a pouch) which is further sealed, e.g., by heat and/or pressure. Where the tissue sample was frozen and dried in a glass vial, the vial is sealed under vacuum with an appropriate inert stopper and the vacuum of the drying apparatus reversed with an inert gas prior to unloading. In either case, the final product is hermetically sealed in an inert gaseous atmosphere.

After rehydration of the ATM (see below), histocompatible, viable cells can be restored to the ATM to produce a permanently accepted graft that may be remodeled by the host. This is generally done after formation as a composite with a non-biologic component and just prior to placing of the ATM in a mammalian subject. Where the matrix has been freeze dried, it will be done after rehydration. In a preferred embodiment, histocompatible viable cells may be added to the matrices by standard in vitro cell coculturing techniques prior to transplantation, or by in vivo repopulation following transplantation. In vivo repopulation can be by the recipient's own cells migrating into the ATM or by infusing or injecting cells obtained from the recipient or histocompatible cells from another donor into the ATM in situ.

The cell types used for reconstitution will depend on the nature of the tissue or organ to which the ATM is being remodeled. For example, the primary requirement for reconstitution of full-thickness skin with an ATM is the restoration of epidermal cells or keratinocytes. For example, cells derived directly from the intended recipient can be used to reconstitute an ATM and the resulting composition grafted to the recipient in the form of a meshed split-skin graft. Alternatively, cultured (autologous or allogeneic) cells can be added to the ATM. Such cells can be, for example, grown under standard tissue culture conditions and then added to the ATM. In another embodiment, the cells can be grown in and/or on an ATM in tissue culture. Cells grown in and/or on an ATM in tissue culture can have been obtained directly from an appropriate donor (e.g., the intended recipient or an allogeneic donor) or they can have been first grown in tissue culture in the absence of the ATM.

The most important cell for reconstitution of heart valves and vascular conduits is the endothelial cell, which lines the inner surface of the tissue. Endothelial cells may also be expanded in culture, and may be derived directly from the intended recipient patient or from umbilical arteries or veins.

Other cells with which the matrices can be repopulated include, but are not limited to, fibroblasts, embryonic stem cells (ESC), adult or embryonic mesenchymal stem cells (MSC), prochondroblasts, chondroblasts, chondrocytes, pro-osteoblasts, osteocytes, osteoclasts, monocytes, pro-cardiomyoblasts, pericytes, cardiomyoblasts, cardiomyocytes, gingival epithelial cells, or periodontal ligament stem cells. Naturally, the ATM can be repopulated with combinations of two more (e.g., two, three, four, five, six, seven, eight, nine, or ten) of these cell-types.

Reagents and methods for carrying out all the above steps are known in the art. Suitable reagents and methods are described in, for example, U.S. Pat. No. 5,336,616.

Particulate ATM can be made from any of the above described non-particulate ATM by any process that results in the preservation of the biological and structural functions described above and, in particular, damage to collagen fibers, including sheared fiber ends, should be minimized. Many known wetting and drying processes for making particulate ATM do not so preserve the structural integrity of collagen fibers.

One appropriate method for making particulate ATM is described in U.S. Pat. No. 6,933,326. The process is briefly described below with respect to a freeze dried dermal ATM but one of skill in the art could readily adapt the method for use with freeze dried ATM derived from any of the other tissues listed herein.

The acellular dermal matrix can be cut into strips (using, for example, a Zimmer mesher fitted with a non-interrupting "continuous" cutting wheel). The resulting long strips are then cut into lengths of about 1 cm to about 2 cm. A homogenizer and sterilized homogenizer probe (e.g., a LabTeck Macro homogenizer available from OMNI International, Warrenton, Va.) are assembled and cooled to cryogenic temperatures (i.e., about −196° C. to about −160° C.) using sterile liquid nitrogen which is poured into the homogenizer vessel. Once the homogenizer has reached a cryogenic temperature, cut pieces of ATM are added to the homogenizing vessel containing the liquid nitrogen. The homogenizer is then activated so as to cryogenically fracture the pieces of the ATM. The time and duration of the cryogenic fracturing step will depend upon the homogenizer utilized, the size of the homogenizing chamber, and the speed and time at which the homogenizer is operated, and are readily determinable by one skilled in the art. As an alternative, the cryofracturing process can be conducted in a cryomill cooled to a cryogenic temperature.

The cryofractured particulate acellular tissue matrix is, optionally, sorted by particle size by washing the product of the homogenization with sterile liquid nitrogen through a series of metal screens that have also been cooled to a cryogenic temperature. It is generally useful to eliminate large undesired particles with a screen with a relatively large pore size before proceeding to one (or more screens) with a smaller pore size. Once isolated, the particles can be freeze dried to ensure that any residual moisture that may have been absorbed during the procedure is removed. The final product is a powder (usually white or off-white) generally having a particle size of about 1 micron to about 900 microns, about 30 microns to about 750 microns, or about 150 to about 300 microns. The material is readily rehydrated by suspension in normal saline or any other suitable rehydrating agent known in the art. It may also be suspended in any suitable carrier known in the art (see, for example, U.S. Pat. No. 5,284,655 incorporated herein by reference in its entirety). If suspended at a high concentration (e.g., at about 600 mg/ml), the particulate ATM can form a "putty", and if suspended at a somewhat lower concentration (e.g., about 330 mg/ml), it can form a "paste". Such putties and pastes can conveniently be packed into, for example, holes, gaps, or spaces of any shape in tissues and organs so as to substantially fill such holes, gaps, or spaces.

One highly suitable freeze dried ATM is produced from human dermis by the LifeCell Corporation (Branchburg, N.J.) and marketed in the form of small sheets as AlloDerm®. Such sheets are marketed by the LifeCell Corporation as rectangular sheets with the dimensions of, for example, 1 cm×2 cm, 3 cm×7 cm, 4 cm×8 cm, 5 cm×10 cm, 4 cm×12 cm, and 6 cm×12 cm. The cryoprotectant used for freezing and drying AlloDerm is a solution of 35% maltodextrin and 10 mM ethylenediaminetetraacetate (EDTA). Thus, the final dried product contains about 60% by weight ATM and about 40% by weight maltodextrin. The LifeCell Corporation also makes an analogous product made from porcine dermis (designated XenoDerm) having the same proportions of ATM and maltodextrin as AlloDerm. In addition, the LifeCell Corporation markets a particulate acellular dermal matrix made by cryofracturing AlloDerm (as described above) under the name Cymetra®. The particle size for Cymetra is in the range of about 60 microns to about 150 microns as determined by mass spectrophotometry.

The particles of particulate or pulverized (powdered) ATM of the invention will be less than 1.0 mm in their longest dimension. Pieces of ATM with dimensions greater than this are non-particulate acellular matrices.

Non-Biologic Component:

The non-biologic component of an implementation of the present invention can generally be comprised of biocompatible synthetic materials, including bioabsorbable polymers, non-bioabsorbable polymers, and metallic alloys or compositions. Various implementations may include a non-biologic component that is biocompatible and bioabsorbable, such that the completed target tissue regeneration does not contain substantial and/or load bearing quantities of the non-biologic component. Utilizing bioabsorbable polymers allows for a transfer of load capacity from the non-biologic component (e.g., the polymer) to the biological component as native tissue regenerates throughout the matrix structure of the biological component.

As used herein, a "biocompatible" composition is one that has the ability to support cellular activity necessary for complete or partial tissue regeneration, but does not stimulate a significant local or systemic inflammatory or immunological response in the host. As used herein, a "significant local or systemic inflammatory or immunological response in the host" is a local or systemic inflammatory or immunological response that partially or completely prevents tissue regeneration.

As used herein, the term "bioabsorbable" is meant to generally indicate a biological mediated degradation process such as enzymatic and cellular processes, and chemically mediated degradation process, of a material within a mammalian body including, but not limited to, degradation processes wherein the degradation products are generally excreted through one of the body's organ systems or the degradation products are incorporated into normal metabolic pathways.

One such bioabsorbable polymer is poly-hydroxybutyrate (a polyhydroxyalkanoate) for example, the TephaFlex polymer produced by Tepha, Inc. of Cambridge, Mass. Other useful bioabsorbable materials include polylactic acid (PLA), polyglycolic acid (PGA), polylactideglycolide acid (PLGA), polydioxanone, or polycaprolactone (PCL).

Further biodabsorbable materials suitable for use in the non-biologic component include polyanhydrides, poly-orthoesters, poly(amino acids), polypeptides, polydepsipeptides, nylon-2/nylon-6coplyamides, poly(alkylene succinates), poly(hydroxyl butyrate) (PHB), poly(butylene diglocolate), poly($\epsilon$-caprolactone) and copolymers, polydihydropyrans, polyphosphazenes, poly(ortho ester), poly(cyano acrylates), modified polysaccharides, cellulose, starch, chitin, modified proteins, collagen, and fibrin. Examples of non-bioabsorbable materials includes nobel metals such as gold.

Other useful synthetic polymers are listed in U.S. Pat. No. 5,885,829 that describes synthetic as well as natural substances useful in tissue regeneration and the disclosure of which is incorporated herein by reference in its entirety.

The form of non-biologic component can range from molded shapes (one contiguous piece of polymer) to textile devices comprised of multiple yams, the yam being either a monofilament or a multifilament structure (such as a braid). Textile manufacturing methods can then make final structures that are knitted, woven, braided, nonwoven, or combinations thereof.

Composite Hybrid Material:

All tissue grafts experience some drop in mechanical characteristics within the first month after implantation. Mechanical performance characteristics can include, without limitation, load performance, elasticity, and stiffness. Recovery of some or all of the mechanical performance characteristics typically progresses over one to two years after implantation.

Typical synthetic materials used in tissue replacement impart an initial load capacity at the time of implantation that can be equal to or higher than natural tissue implants. But synthetic tissue implants typically experience a continual and at times significant loss in load capacity over the first two years after implantation.

Natural fiber tissue implants, such as autografts and allografts, experience a significant drop in load capacity during about the first month after implantation, with an ultimate recovery of load capacity and other mechanical performance characteristics of between 50-60% of the starting strength of the natural graft tissue.

Various implementations of the hybrid composite tissue of the present invention combine the benefits of typical synthetic polymer tissue grafts—having relatively higher initial mechanical performance characteristics—with the prohealing and better long-term mechanical characteristics of natural tissue grafts. The hybrid tissue can performs as a summation of the individual components. The hybrid tissue can also perform better than a summation of the individual components. For example, a typical synthetic implant experiences degradation with decreasing physical performance over time. The hybrid composite tissue of the present development provides a layer of biomatrix around or over the synthetic component, thereby slowing the degradation from that experienced by a typical, uncoated synthetic implant.

It has been found that the first biologic component and the second non-biologic component can be constructed to optimize the mechanical performance parameters desired for the specific tissue being replaced. For example, in constructing a hybrid tissue for ligament replacement, it can be desirable to have an ultimate load failure of approximately 1800 N. If the constructed first component biomatrix material provides an ultimate failure load of only 400 N, then the synthetic second component can be configured to provide the remaining 1400 N to produce a hybrid composite tissue graft having the desired performance characteristics. Similarly, if the desired stiffness for the ACL replacement graft is 200 N/mm and the biomatrix of the first component provides only 50 N/mm, then the polymeric of the second component can be configured to provide the remaining stiffness of 150 N/mm.

Figure 1:
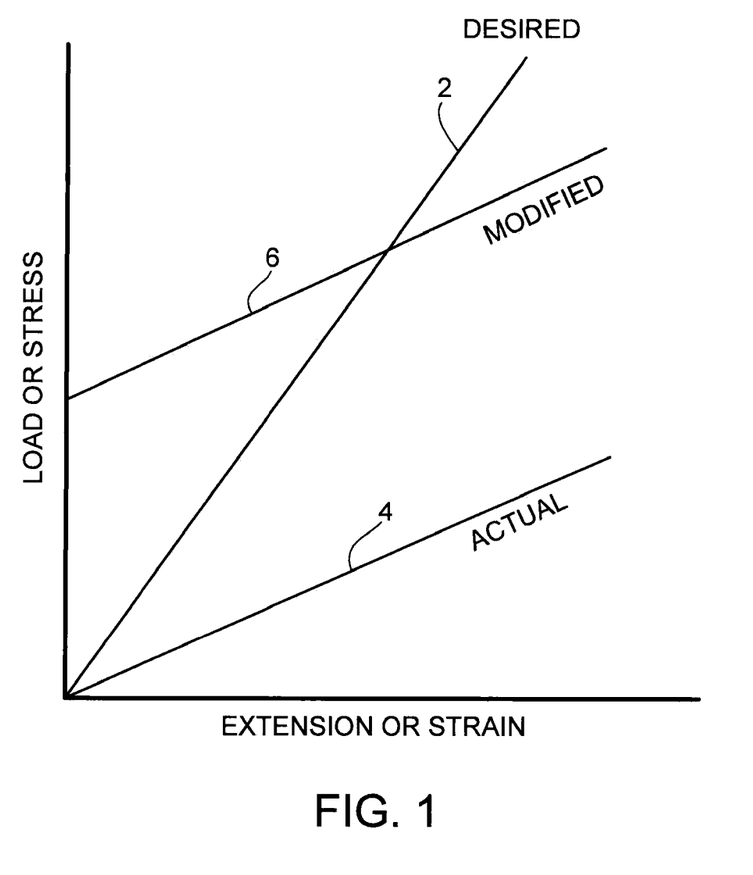
FIG. 1 shows a graph illustrating biomechanical characteristics of implementations of the present invention.

FIG. 1 illustrates an exemplary stress-strain curve of various tissue grafts. Line 2 illustrates a desired curve for an ideal graft. Line 4 illustrates an exemplary actual stress strain curve for either a synthetic or natural tissue graft. As can be seen the actual grafts are not capable of reaching the desired stress levels for the same amount of strain sought in a desired graft.

It has been found that preparing a hybrid graft of both biologic and non-biologic material (e.g., preparation of a weave, or of a braid or of a crimp, or of some other configuration such as a layered or rolled configuration), raises the stress-strain curve for the modified hybrid material along the y axis. Consequently, line 6 illustrates a modified hybrid graft having improved load capacity performance over actual synthetic or biological grafts.

Figure 2:
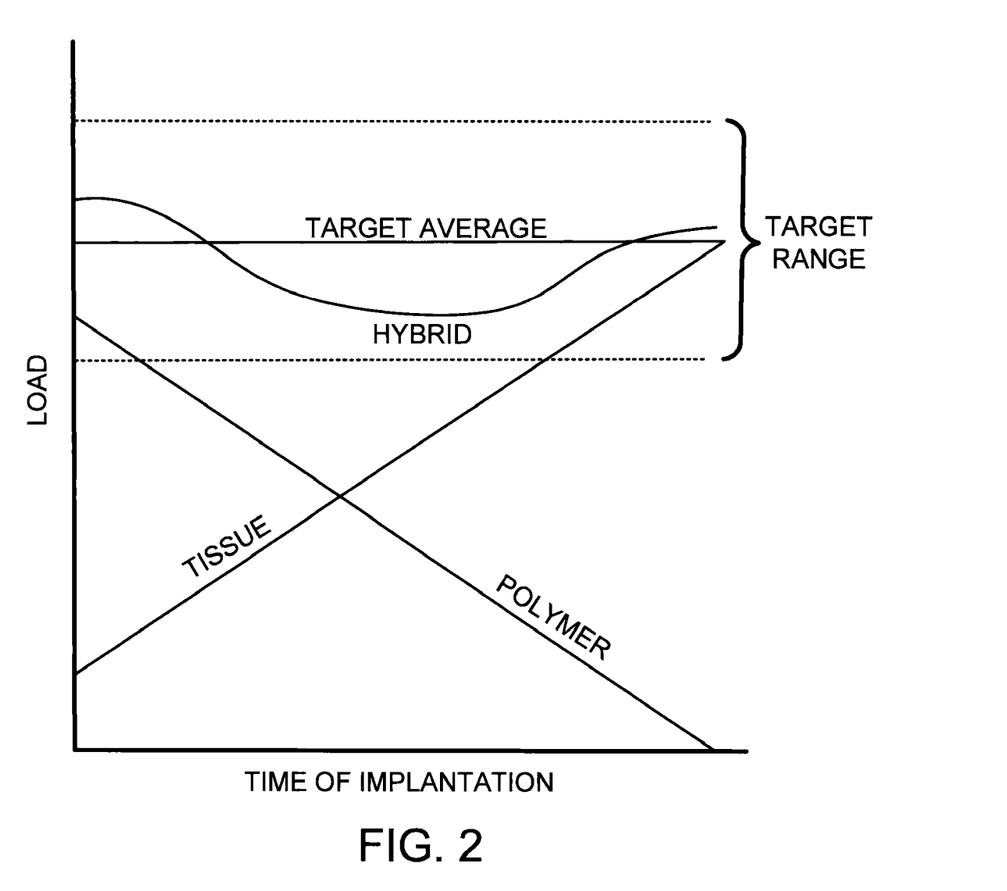
FIG. 2 shows a graph illustrating biomechanical characteristics of implementations of the present invention.

FIG. 2 illustrates the concept of functional target loading of the construct hybrid graft and is a plot of the load capacity versus the time since implantation of the composite hybrid graft. As can be seen, biological tissue alone has a relatively low load capacity at the time of implantation. As the body subsequently heals, the load-bearing capacity increases over time. Conversely, a polymer graft's load-bearing capacity is relatively high initially upon implantation, but it decreases subsequently. It has been found that a hybrid composite graft consistent with the present development (labeled "Hybrid") comprising both a biological component having a biomatrix and a man-made non biological component (such as a polymer) remains relatively stable in load-bearing capacity over time (that is, the load bearing capacity starts out, and remains, in the "Target Range").

It will be appreciated that the non-biologic component can be married to the biologic component in a variety of ways, for example, tissue around non-biologic component (as exemplified in FIG. 3), non-biologic component around tissue, or tissue embedded within or coating a knit, weave, braid or other textile of the non-biologic component. Additionally, to assure load sharing between, for example, the non-biologic component and the tissue component, the two components can be co-mingled or the separate components can be layered and rolled tightly around one anther. The tightly connected layered construct leverages the micro and nano structural interface between the non-biologic component and the biologic component to create a frictional hold. Compressive force may be added to the layered construct by including securing straps, similar to a belt and hoop design.

Figure 3:
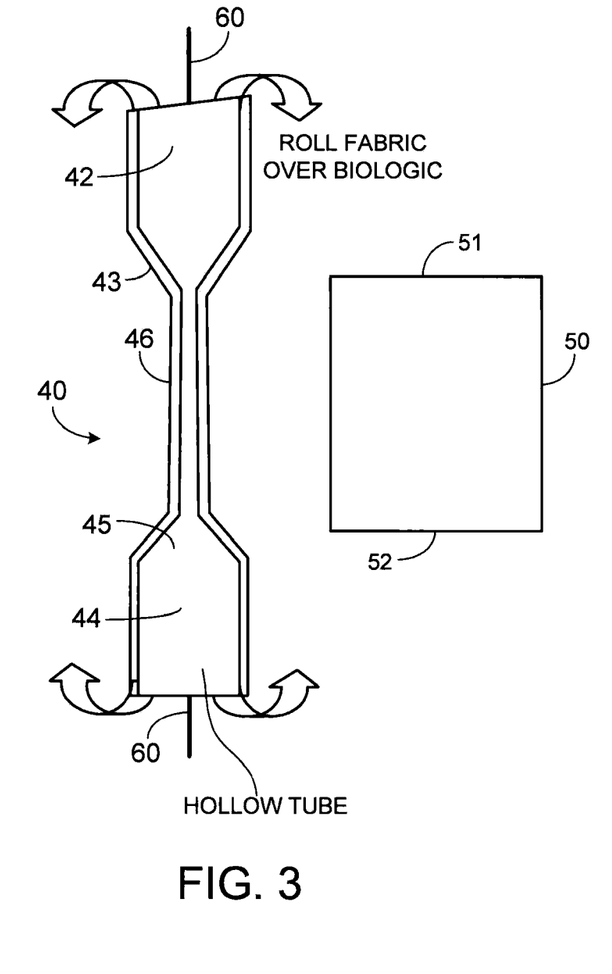
FIGS. 3 and 3A shows an implementation of the present invention.

FIG. 3 depicts one exemplary implementation of the hybrid composite tissue graft. A tubular non-biologic component 40 is provided having an upper portion 42, an upper taper region 43, a lower portion 44, a lower taper region 45, and a neck portion 46. Also provided is a biologic component 50 illustrated as a sheet with an upper edge 51 and a lower edge 52. In an exemplary construction, the biologic component 50 is wrapped around neck portion 46 of non-biologic component 40 so that upper edge 51 is in contact proximal to or with upper taper region 43 and lower edge 52 is in contact proximal to or with lower taper region 45. Biological component 50 can wrap or encircle neck portion 46 one or more times to form a multi-layer wrap. For example biological component 50 can wrap around neck portion 46 of non-biological component 40 one time, two times, three times, four times, five times, or more. Biological component 50 can similarly wrap around upper portion 42 and lower portion 43 of non-biological component 40 one or more times.

Figure 3A:
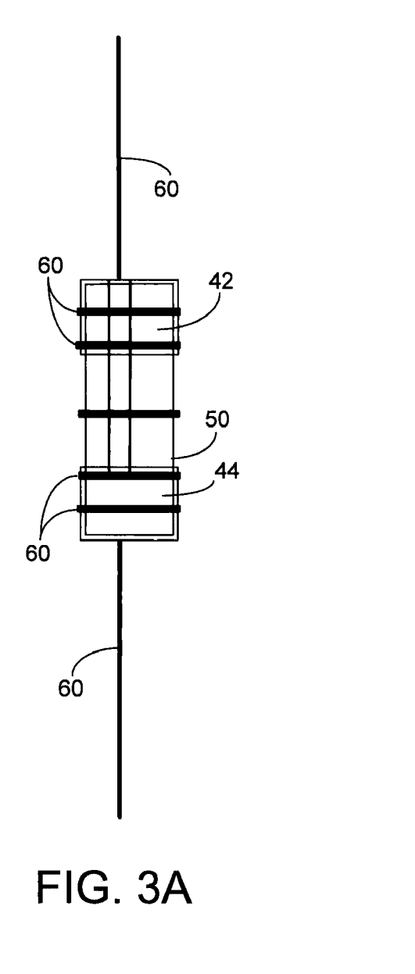

After wrapping biologic component 50 around non-biological component 40, upper portion 42 of non-biological component 40 is rolled or folded over wrapped biological component 50 and toward lower portion 44 such that at least some of upper portion 42 extends below the upper taper region 43 and overlaps neck portion 46. Similarly, lower portion 44 is rolled or folded over biological component 50 and toward upper portion 42 such that at least some of lower portion 44 extends above lower taper region 45 and overlaps neck portion 46, as depicted in FIG. 3A.

A further implementation includes one or more securing straps 58, and tethers 60. Securing straps 58 provide compressive force to the rolled hybrid composite graft better leveraging the frictional contact and bond of the micro and nano surface structure of the biological component against the non-biological component. Securing straps 58 can be constructed of the same material as non-biological component 40.

Tethers 60 assist during implantation of the device. Tethers 60 can be used to pull the tissue/non-biologic component combined device into the bone tunnel. Tethers 60 can be made from the same material as the textile portion of the graft or from other materials such as stainless steel or non-bioabsorbable polymers. Tethers 60 could be used to aid during the construction phase of the hybrid device. For example, tethers 60 can be used to anchor the non-biological component 40 while the biologic component 50 is wrapped around the non-biologic component 40. Tethers 60 can be woven, knitted, or braided into the non-biologic component 40 or the fully assembled hybrid graft. Tethers 60 can be integral to the non-biological component 40 or can be configured to detach from the non-biologic component 40 once tethers 60 have served their purpose. Tethers 60 can be further used as a radiopaque marker.

Figure 4:
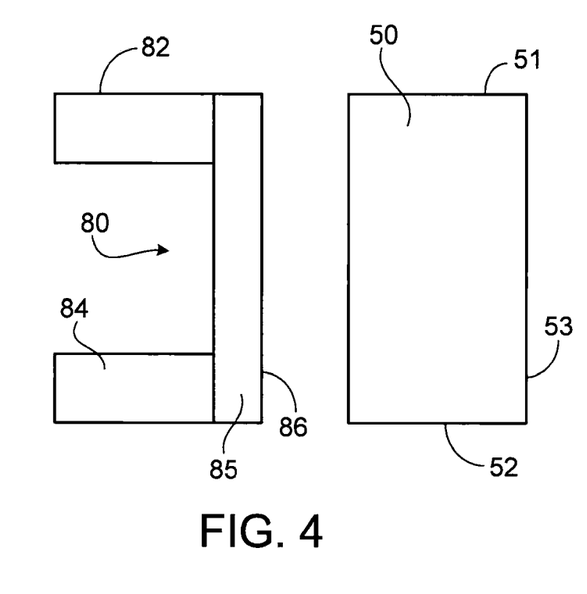
FIGS. 4 and 4A show an implementation of the present invention.

An alternate construction of an implantation replaces the hollow tube of the non-biologic component 40 discussed above with a flat sheet of non-biologic component, as illustrated in FIG. 4. Non-biologic component 80, includes an upper portion 82 a lower portion 84, a neck portion 85 and a neck lateral edge 86. Upper portion 82 and lower portion 84 may be the same or different non-biological components as neck portion 85. For example, in one implementation, neck portion 85 can comprise a high tensile strength textile of a bioabsorbable polymer while upper portion 82 and lower portion 84 can comprise a relatively lower tensile strength textile of a bioabsorbable polymer. Non-biologic component 80 can also comprise non-textile polymers as previously described.

Referring still to FIG. 4, biological component 50 is provided as a flat sheet of biological material comprising an acellular tissue matrix having an upper edge 51, a lower edge 52 and a lateral edge 53. Non-biologic component 80 is placed on top of biologic component 50 such that neck lateral edge 86 of non-biologic component 80 aligns with lateral edge 53 of biological component 50. The two layered components are then rolled such that neck lateral edge 86 and lateral edge 53 remain aligned and form the innermost portion of the roll.

Figure 4A:
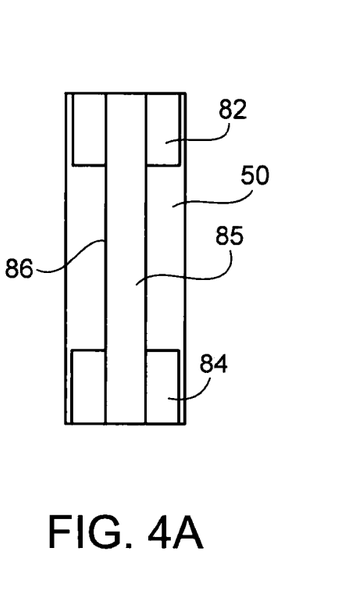

FIG. 4A shows a rolled hybrid composite tissue graft constructed as described above with the biological component 50 forming the outside surface of the rolled structure and neck lateral edge 86 forming the inner most portion of the rolled structure. Upper portion 82 and lower portion 84 form a multi-layered non-biologic material within the rolled structure and can provide added strength and material to secure the hybrid composite tissue graft to the surrounding native tissue, for example, by interference screws.

In an implementation of the hybrid tissue, the implant closely matches the ligament size (length, width, thickness) of the natural structure it will replace. For example, for an ACL, the hybrid device can be about 6-12 in diameter for a unibody device or 3 to 6 mm in diameter if separated into two bundles. Matching the size of the tissue implant with the native tissue to be removed reduces complications. Within the body, specific ligament sizes slide and fit between bony structures. A ligament which is too small may not distribute stress evenly and too large a ligament may interfere or rub against one or both bony structures.

It will be appreciated that actual sizes of the hybrid composite graft of the present invention can be customized to the patient and the tissue being replaced. For example, one or more rolls of biological and non-biological components can be added or deleted by varying the size or length of the individual components. For example, the longer the pre-rolled composite construct, the more rolls are possible, thereby producing a finished hybrid composite tissue graft having a greater diameter. Alternatively the number of layers of individual components can be altered to adjust the final size of the hybrid graft. For example, a composite construct comprising a tissue layer, a polymer layer, and another tissue layer would offer a larger diameter hybrid graft than a composite construct of only two layers.

Figure 5:
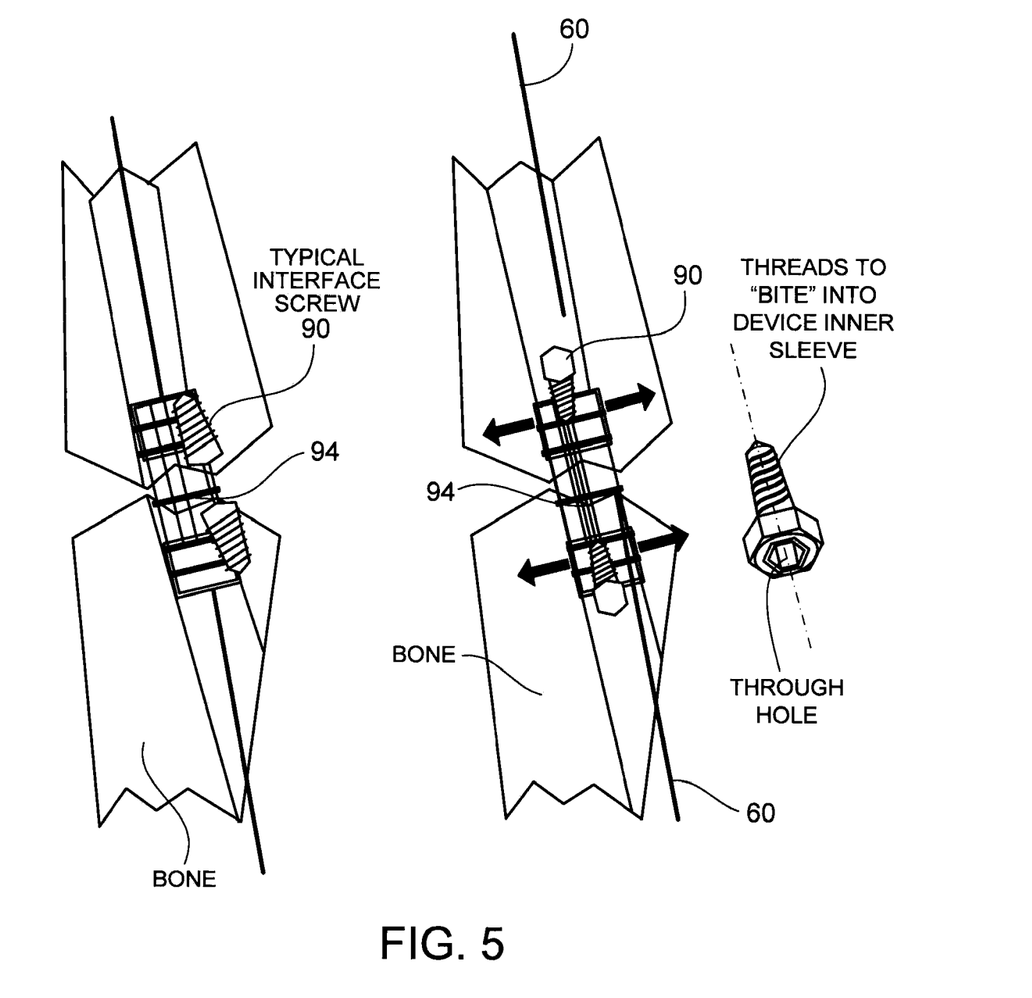
FIG. 5 shows an implementation of the present invention.

Also, included in the various implementations of the present invention are techniques to anchor or fix the artificial hybrid composite tissue graft to the implantation site. For example, in an ACL replacement, the use of simple interference screws is typical for anchoring cadaver or autograft materials. In an implementation an interference screw is provided that anchors the hybrid composite tissue graft from inside of the graft structures. This is shown in FIG. 5, wherein interference screw 90 is inserted into the core of hybrid graft 94 such that as interference screw 90 advances, screw 90 expands the diameter of hybrid graft 94 to exert outwardly radial pressure against the resisting bone tunnel. Alternatively, standard interference screws may be used to fix the hybrid graft. Other common fixation devices may be used, including cross-pins, endobuttons, sutures, or staples.

Interference screws can be made of Titanium, Stainless Steel, biodegradable metals, biodegradable or bioabsorbable polymers such as PGA, PLA, PLGA, or PCL. A typical interference screw would be a Smith and Nephew, Andover Mass., 01810, screw type RCI Screw.

Example

A hybrid composite tissue graft suitable for ACL replacement was made having a first biological component including a biomatrix. The biomatrix comprised an acellular tissue matrix consistent with the acellular tissue matrix described herein. The biomatrix was provided as a single sheet of material.

The hybrid composite tissue graft also included a second non-biologic component made of polyhydroxybutyrate, (a polyhydroxylalkanoate) for example, TephaFlex polymer produced by Tepha, Incorporated of Cambridge, Mass. The second component was also provided as a single sheet of material of similar dimensions as the first biologic component.

The composite graft was constructed by overlaying the second component on top of the first component and rolling the layered sheets into a roll of composite material that resulted in multiple layers of the first component and the second component from the center of the roll outward to the outer layer of the roll. The rolled composite material had a diameter of approximately 8 mm.

A native ACL typically has biomechanical performance characteristics within the following ranges: Failure Load (1200-2400 N); Stiffness (150-300 N/mm); Failure Stress (18-28 MPa); Strain at Failure (20-35%); and Modulus of Elasticity (75-180 Mpa). In order to match the natural mechanical and biological properties of native ACL tissue, each component in the hybrid device was selected and constructed to meet specific design requirements. The non-biological component of the hybrid tissue had a modulus of elasticity of about 140 MPa, a maximum rupture load or ultimate load failure of about 1200 N, and degradation resistance through 9 to 16 months before construction of the hybrid composite tissue graft.

The biologic component at the time of implantation had a modulus of elasticity of about 55 MPa, and a maximum load at rupture of approximately 600 N before construction of the composite hybrid tissue graft.

After the composite graft was assembled the completed implant had a maximum load rupture of approximately 1400 N before implantation. The ultimate failure load decreased after implantation though steadily increased over time as native cells proliferated through the biomatrix. The implant had an ultimate failure load of approximately 600 N within four months of implantation, approximately 400 N within eight months of implantation and approximately 1000 N within 12 months of implantation. The hybrid material for the ACL replacement had a stiffness of approximately 85 N/mm before implantation, approximately 106 N/mm within four months of implantation, approximately 78 N/mm within eight months of fixation, and approximately 176 N/mm within twelve months of fixation.

ACL replacement with the hybrid tissue produced continuous tissue from the bone connection through the biomatrix to the opposite bone connection after four months, eight months and twelve months, of implantation in 5 out of 5 test cases. Tissue only grafts typically fail to produce continuous tissue growth 2 out of 5 times within 4 and 8 months of implantation. Synthetic only grafts typically fail to produce continuous tissue growth 1 out of 5 times within 4, 8 and 12 months of implantation.

Figure 6:
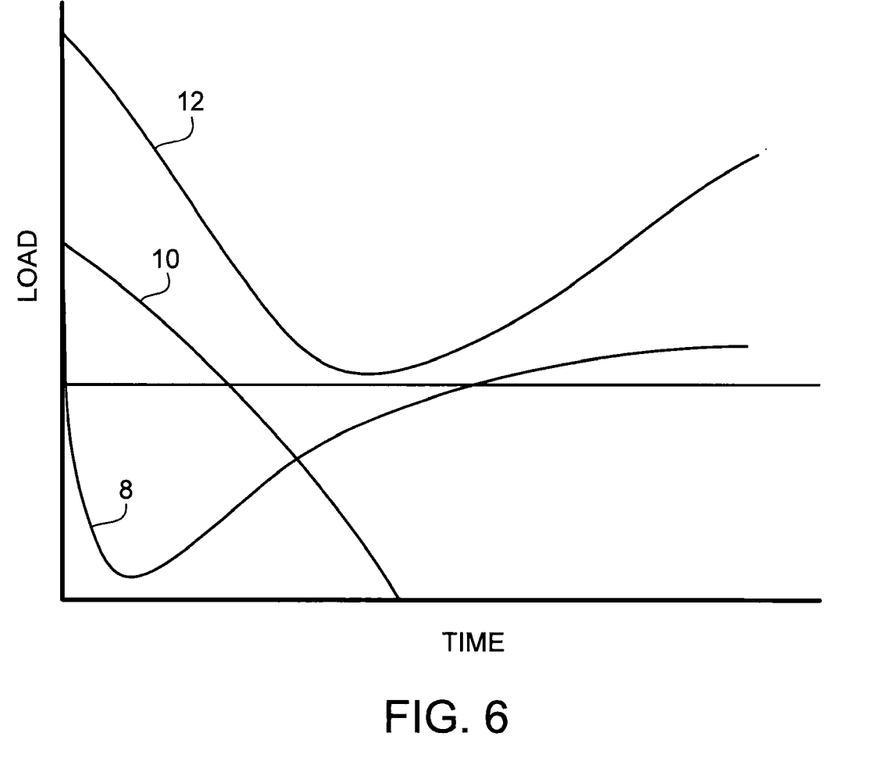
FIG. 6 shows a graph illustrating biomechanical characteristics of an exemplary implementation of the present invention.

FIG. 6 depicts the load capacity over time of the first component, the second component and the hybrid graft of the exemplary implementation. As shown, the first component, line 8, showed a drop in load capacity immediately following implantation with an increase in load capacity thereafter as native cells proliferated throughout the biomatrix. Line 10 illustrates the initially high load capacity of the second component after implantation with a steady decrease in load capacity as the second component degraded over time. Line 12 shows the load capacity of the hybrid graft containing both the first component and the second component.

Although the present invention has been described in considerable detail with reference to certain implementations, other implementations are possible. For example, implementations of the hybrid tissue structure can be used for many applications where soft tissues needs to be replaced and yet provide specific load-carrying or biomechanical characteristics, including ligament, tendon or soft tissue replacement about the knees, ankles, shoulders, neck, and spine. Other hybrid systems can be developed utilizing the same basic ideas as described above. Examples include: artificial meniscus replacement or repair; abdominal wall (e.g., hernia) repair; cartilage repair in, for example, knees, shoulders and hips; joint resurfacing (instead of removing joints, the joint articulating surface can simply be covered with a hybrid tissue reinforced with fabric using appropriately designed anchors or sutures); and pace maker pouches (a simple bag/pouch used to contain pacers or pain manager systems would make periodic replacement much simpler and would create a more stable anchor pacer implant). Therefore the spirit and scope of the appended claims should not be limited to the specific implementations contained herein.

What is claimed is:

1. An implantable medical device, comprising:
a composite material comprising:
a sheet of an acellular tissue matrix; and
a non-biological component including an upper portion, a lower portion, and a neck portion between the upper portion and the lower portion,
wherein the sheet of the acellular tissue matrix wraps around the neck portion of the non-biological component between the upper portion and the lower portion and covers at least a portion of a surface of the non-biological component to form an elongated composite having a predetermined target load capacity approximating the load capacity of a native human ligament to be replaced by the elongated composite,
wherein at least one of (i) the upper portion of the non-biological component is folded over in the direction of the lower portion of the non-biological component or (ii) the lower portion of the non-biological component is folded over in the direction of the upper portion of the non-biological component, to overlap a portion of the wrapped sheet of the acellular tissue matrix with the non-biological component while maintaining a central portion of the wrapped sheet of the acellular tissue matrix exposed between the upper and lower portions of the non-biological component, and wherein the non-biological component has a higher tensile load capacity than the sheet of the acellular tissue matrix at the time of implantation, and the sheet of the acellular tissue matrix has a higher load capacity than the non-biological component after implantation and following growth of native cells within the acellular tissue matrix, such that the load capacity of the composite material is within the target load capacity range at the time of implantation and also following growth of native cells within the acellular tissue matrix.

2. The medical device of claim 1, wherein the sheet of the acellular tissue matrix overlays the non-biological component for substantially all of the composite material.

3. The medical device of claim 1, wherein the non-biological component comprises a bioabsorbable polymer.

4. The medical device of claim 1, wherein the non-biological component comprises a biocompatible metal.

5. The medical device of claim 1, wherein the non-biological component comprises polyhydroxybutyrate, polyactic acid, polyactideglycolide acid, polydioxanone or polycaprolactone.

6. The medical device of claim 1, wherein the non-biological component is a textile including non-biologic material, the textile being a knit, a weave, a braid, a nonwoven structure, or a combination of knit, weave, braid or nonwoven structures.

7. The medical device of claim 6, wherein the non-biological component comprises a monofilament of non-biological material.

8. The medical device of claim 6, wherein the non-biological component further comprises a braided or spun multifilament yarn.

9. The medical device of claim 6, wherein the sheet of the acellular tissue matrix is integrated into the textile structure of the non-biological component.

10. The medical device of claim 1, wherein the composite material forms a sheet, a cylinder, a solid tube, a hollow tube or a rolled sheet.

11. The medical device of claim 1, further comprising a tether portion.

12. The medical device of claim 1, wherein the non-biological component has a higher stiffness than the sheet of biological component at the time of implantation.

13. The medical device of claim 12, wherein the stiffness of the composite material substantially matches the stiffness of the native human ligament to be replaced by the composite material.

14. The medical device of claim 13, wherein the native human ligament is an anterior cruciate ligament.

15. The medical device of claim 1, further comprising at least one screw.

16. The medical device of claim 15, further including multiple tethers wrapped around an outer surface of the composite material.

17. The medical device of claim 1, wherein the target load capacity approximates the load capacity of a native anterior cruciate ligament to be replaced by the composite material.

18. The medical device of claim 1, wherein the non-biological component comprises polyhydroxybutyrate.

19. The medical device of claim 1, wherein at least one of the upper portion or the lower portion of the non-biological component folded over and overlapping the portion of the wrapped sheet of the acellular tissue matrix imparts a compressive force on the sheet of biological component to maintain the sheet of the acellular tissue matrix wrapped around the portion of the surface of the non-biological component.

20. The medical device of claim 1, wherein the non-biological component defines a longitudinal axis, and wherein at least one of (i) the upper portion of the non-biological component or (ii) the lower portion of the non-biological component, is folded over along the longitudinal axis to overlap the portion of the wrapped sheet of the acellular tissue matrix with the non-biological component while maintaining the central portion of the wrapped sheet of the acellular tissue matrix exposed between the upper and lower portions of the non-biological component.

* * * * *